US011962980B2

(12) United States Patent
Rehmann et al.

(10) Patent No.: US 11,962,980 B2
(45) Date of Patent: *Apr. 16, 2024

(54) HEARING EVALUATION SYSTEMS AND METHODS IMPLEMENTING A SPECTRO-TEMPORALLY MODULATED AUDIO SIGNAL

(71) Applicant: SONOVA AG, Staefa (CH)

(72) Inventors: Julia Rehmann, Schmerikon (CH); Stefan Klockgether, Hombrechtikon (CH)

(73) Assignee: Sonova AG, Staefa (CH)

( * ) Notice: Subject to any disclaimer, the term of this patent is extended or adjusted under 35 U.S.C. 154(b) by 222 days.

This patent is subject to a terminal disclaimer.

(21) Appl. No.: 17/667,072

(22) Filed: Feb. 8, 2022

(65) Prior Publication Data

US 2022/0240033 A1 Jul. 28, 2022

Related U.S. Application Data

(63) Continuation-in-part of application No. 17/161,500, filed on Jan. 28, 2021.

(51) Int. Cl.
*H04R 25/00* (2006.01)
*A61B 5/12* (2006.01)

(52) U.S. Cl.
CPC .......... *H04R 25/70* (2013.01); *H04R 25/505* (2013.01); *H04R 2225/43* (2013.01)

(58) Field of Classification Search
None
See application file for complete search history.

(56) References Cited

U.S. PATENT DOCUMENTS

2019/0379985 A1* 12/2019 Thomsen ............. H04R 25/353
2022/0007116 A1* 1/2022 Lunner ................. H04R 25/30

FOREIGN PATENT DOCUMENTS

CN 105357619 10/2018
DE 10048157 1/2009
(Continued)

OTHER PUBLICATIONS

Mehraei, Golbarg. "Spectrotemporal modulation sensitivity for hearing-impaired listeners: Dependence on carrier center frequency and the relationship to speech intelligibility". J Acoust Soc Am. Jul. 2014; 136(1): 301-316. 16 pages. (Year: 2014).*

(Continued)

*Primary Examiner* — Qin Zhu
(74) *Attorney, Agent, or Firm* — ALG Intellectual Property, LLC

(57) ABSTRACT

An exemplary system includes a memory storing instructions and a processor communicatively coupled to the memory. The processor may be configured to execute the instructions to present a spectro-temporally modulated audio signal to a user. The spectro-temporally modulated audio signal may be modulated within both a frequency domain and a time domain. The processor may be further configured to execute the instructions to adjust a modulation depth of the spectro-temporally modulated audio signal while the spectro-temporally modulated audio signal is being presented to the user, determine, during the adjusting of the modulation depth, a modulation detection threshold that corresponds to a minimum modulation depth at which the user is able to perceive modulation of the spectro-temporally modulated audio signal, and determine, based on the modulation detection threshold, a hearing capability of the user.

20 Claims, 9 Drawing Sheets

(56) References Cited

FOREIGN PATENT DOCUMENTS

| EP | 1686566 | 8/2006 |
|----|---------|--------|
| EP | 1441562 | 3/2010 |
| EP | 3085109 | 10/2018 |
| WO | 2015128411 | 9/2015 |

OTHER PUBLICATIONS

Andersen, et al.,"Audiblity Extender", Widex.(2006).
Angelo, et al.,"Oticon Frequency Lowering: Access to High-Frequency Speech Sounds with Speech Rescue Technology", Whitepaper 2015—Oticon Frequency Lowering.
Bagatto, et al.,"Clinical Protocols for Hearing Instrument Fitting in the Desired Sensation Level Method", Trends in Amplification, 2005, vol. 9, 199-226, doi: 10.1177/108471380500900404.
Bentler, et al.,"Nonlinear Frequency Compression in Hearing Aids: Impact on Speech and Language Development", Ear Hear, 2014; 35(4): e143-e152.
Galster, et al.,"Spectral iQ: Audibly Improving Access to High-Frequency Sounds", Audiology Online, 2012, Starkey.
Glasberg, et al.,"Derivation of Auditory Filter Shapes from Notched-Noise Data", 1990, Hearing Research 47, 103-138, doi: 10.1016/0378-5955(90)90170-T.
Haastrup, et al.,"Improving High Frequency Audibility with Sound Shaper", Resound 2014.
Hopkins, et al.,"The effects of age and cochlear hearing loss on temporal fine structure sensitivity, frequency, selectivity, and speech reception in noise", Hopkins & Moore 2011, J. Acoust. Soc. Am. 130, 334-349 , doi: 10.1121/1.3585848.
Kuriger, et al.,"Frequency Composition: A New Approach to Frequency Lowering, Bernafon", Dec. 2012.
Larsby, et al.,"A Method for Evaluating Temporal, Spectral and Combined Temporal-Spectral Resolution of Hearing", 1998, Scand. Aud. 27, 3-12, DOI: 10.1080/010503998419641.
Litvak,L.M. et al.,"Relationship between perception of spectral ripple and speech recognition in cochlear implant and vocoder listeners", J. Acoust. Soc. Am. 122 (2007), pp. 982 to 991.
Mehraei, et al.,"Spectrotemporal modulation sensitivity for hearing-impaired listeners: Dependence on carrier center frequency and the relationship to speech intelligibility", 2014, J. Acoust. Soc. Am. 136, 301-316, doi: 10.1121/1.4881918.
Rehmann, et al.,"Sound Recover2—the adaptive frequency compression algorithm", Phonak Insight, Apr. 2016.
Scollie, et al.,"Fitting Frequency-Lowering Signal Processing Applying the American Academy of Audiology Pediatric Amplification Guideline: Updates and Protocols, Journal of the American Academy of Audiology"; vol. 27, No. 3, Mar. 2016, pp. 219-236(18)).
Serman, et al.,"White Paper: micon Frequency Compression", Siemens AG 2012.
Wolfe, et al.,"Preliminary evaluation of a novel non-linear frequency compression scheme for use in children", Ear Hear. Jul.-Aug. 2014; 35(4):e143-e152.

* cited by examiner

HEARING EVALUATION SYSTEMS AND METHODS IMPLEMENTING A SPECTRO-TEMPORALLY MODULATED AUDIO SIGNAL

RELATED APPLICATIONS

This application is a continuation-in-part of U.S. patent application Ser. No. 17/161,500, filed Jan. 28, 2021, which is hereby incorporated by reference in its entirety.

BACKGROUND INFORMATION

Hearing devices (e.g., hearing aids) are used to improve the hearing capability and/or communication capability of users of the hearing devices. Such hearing devices are configured to process a received input sound signal (e.g., ambient sound) and provide the processed input sound signal to the user (e.g., by way of a receiver (e.g., a speaker) placed in the user's ear canal or at any other suitable location).

When a hearing device is initially provided to a user, and during follow-up tests and checkups thereafter, it is usually necessary to "fit" the hearing device to the user. Fitting of a hearing device to a user is typically performed by an audiologist or the like who presents various stimuli having different loudness levels to the user. The audiologist relies on subjective feedback from the user as to how such stimuli are perceived. The subjective feedback may then be used to generate a hearing profile (e.g., an audiogram) that indicates individual hearing thresholds and loudness comfort levels of the user. Adjustments may be made based on the hearing profile to specifically tailor parameters (e.g., prescriptive gain) of the hearing device to the user.

Although a user's hearing thresholds indicated in a hearing profile are useful in tailoring parameters of a hearing device to the user, end-user feedback and studies have shown that benefits gained from a hearing device fitted with regard to such hearing thresholds may vary greatly. This may be true even within groups of users with almost identical hearing profiles. Accordingly, when it comes to fitting parameters of a hearing device to a user, a typical hearing profile fails to provide sufficient information on individual hearing loss and/or residual hearing of the user.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
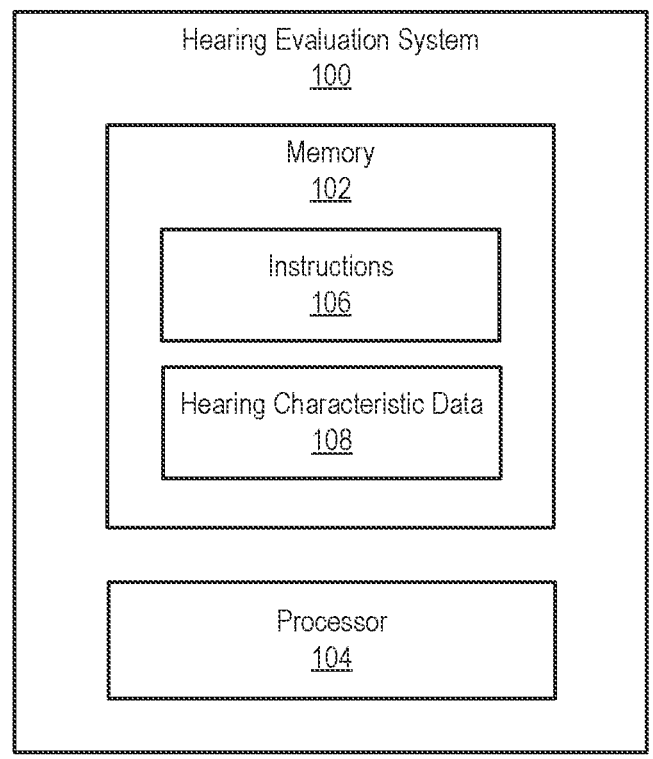
FIG. 1 illustrates an exemplary hearing evaluation system according to principles described herein.

Hearing evaluation systems and methods implementing a spectro-temporally modulated audio signal are described herein. As will be described in more detail below, an exemplary system comprises a memory storing instructions and a processor communicatively coupled to the memory. The processor may be configured to execute the instructions to present a spectro-temporally modulated audio signal to a user (e.g., a user of a hearing device, a candidate for a hearing device, and/or any other person for whom it may be desired to determine a hearing capability). The spectro-temporally modulated audio signal may be modulated simultaneously within both the frequency domain and the time domain. The processor may be further configured to execute the instructions to adjust a modulation depth of the spectro-temporally modulated audio signal while the spectro-temporally modulated audio signal is being presented to the user, determine, during the adjusting of the modulation depth, a modulation detection threshold that corresponds to a minimum modulation depth at which the user is able to perceive modulation of the spectro-temporally modulated audio signal, and determine, based on the modulation detection threshold, a hearing capability of the user. As will be described herein, the hearing capability of the user may correspond to a spectral sensitivity of the user within a frequency range associated with the spectro-temporally modulated audio signal. Additionally or alternatively, the hearing capability of the user may correspond to one or more hearing thresholds of the user that may be estimated based on the modulation detection threshold.

As used herein, a "spectro-temporally modulated audio signal" may refer to any suitable audio signal that is modulated simultaneously both in a frequency domain and a time domain. A spectro-temporally modulated audio signal may implement any suitable carrier noise to which modulation may be applied (e.g., multiplied). For example, the carrier noise may be white noise, pink noise, and/or any other suitable form of tone complex. A modulation depth of a spectro-temporally modulated audio signal may be adjusted in any suitable manner such as described herein to facilitate determining of a modulation detection threshold. As used herein, a "modulation detection threshold" corresponds to a minimum modulation depth at which a user is able to perceive modulation of the spectro-temporally modulated audio signal. At a modulation depth higher than the modulation detection threshold, the user is able to perceive the characteristic modulation of the spectro-temporally modulated audio signal. However, at a modulation depth less than the modulation detection threshold, the user is only able to perceive the spectro-temporally modulated audio signal as constant noise. As such, spectro-temporally modulated audio signals such as those described herein are different than audio signals used in pure-tone audiometry where a loudness level of the audio signals is adjusted to determine hearing thresholds of a user. Specific examples of spectro-temporally modulated audio signals are described herein.

By providing hearing evaluation systems and methods such as those described herein, it is possible to provide improved individualized fitting (e.g., improved frequency lowering, improved gain adjustment, etc.) of a hearing device to a user based on spectral sensitivity. In addition, the methods and systems described herein provide a simple and fast process to determine spectral sensitivity that is feasibly implemented in the everyday practice of a hearing care professional such as an audiologist or the like at a hearing device fitting facility. Moreover, with the hearing evaluation systems and methods described herein, it could be possible to detect and address hidden hearing loss and/or other hearing characteristics that are not otherwise discernable solely by pure-tone audiometry. For example, with the hearing evaluation systems and methods described herein, it may be possible to use modulation detection thresholds to estimate one or more hearing thresholds of a user in circumstances (e.g., loud hearing environments) where using pure-tone audiometry to determine such hearing thresholds is not feasible. Other benefits of the hearing evaluation systems and methods described herein will be made apparent herein.

As will be described further herein, hearing evaluation systems and methods such as those described herein may be used to more accurately fit a hearing device to a user as compared to known fitting systems. As used herein, a "hearing device" may be implemented by any device configured to provide or enhance hearing to a user. For example, a hearing device may be implemented by a hearing aid configured to amplify audio content to a user, a sound processor included in a cochlear implant system configured to apply electrical stimulation representative of audio content to a user, a sound processor included in a stimulation system configured to apply electrical and acoustic stimulation to a user, or any other suitable hearing prosthesis or combination of hearing prostheses. In some examples, a hearing device may be implemented by a behind-the-ear ("BTE") component configured to be worn behind an ear of a user. In some examples, a hearing device may be implemented by an in-the-ear ("ITE") component configured to at least partially be inserted within an ear canal of a user. In some examples, a hearing device may include a combination of an ITE component, a BTE component, and/or any other suitable component.

FIG. 1 illustrates an exemplary hearing evaluation system 100 ("system 100") that may be implemented according to principles described herein. As shown, system 100 may include, without limitation, a memory 102 and a processor 104 selectively and communicatively coupled to one another. Memory 102 and processor 104 may each include or be implemented by hardware and/or software components (e.g., processors, memories, communication interfaces, instructions stored in memory for execution by the processors, etc.).

Memory 102 may maintain (e.g., store) executable data used by processor 104 to perform any of the operations associated with implementing a spectro-temporally modulated audio signal. For example, memory 102 may store instructions 106 that may be executed by processor 104 to perform any of the operations associated with system 100 described herein. Instructions 106 may be implemented by any suitable application, software, code, and/or other executable data instance.

Memory 102 may also maintain any data received, generated, managed, used, and/or transmitted by processor 104. For example, memory 102 may maintain hearing characteristic data 108 that may be representative of any information associated with hearing loss characteristics of a user of a hearing device (e.g., hearing profiles, hearing thresholds, modulation detection thresholds, etc.). Memory 102 may also maintain additional data including, but not limited to, user interface information, notification information, spectro-temporally modulated audio signal information, and/or any other suitable information. In addition, memory 102 may maintain any data suitable to facilitate communications (e.g., wired and/or wireless communications) between system 100 and a hearing device, such as those described herein. Memory 102 may maintain additional or alternative data in other implementations.

Processor 104 may be configured to perform (e.g., execute instructions 106 stored in memory 102 to perform) various processing operations associated with implementing a spectro-temporally modulated audio signal. Such processing operations may include presenting a spectro-temporally modulated audio signal to a user, adjusting a modulation depth of the spectro-temporally modulated audio signal while the spectro-temporally modulated audio signal is being presented to the user, determining, during the adjusting of the modulation depth, a modulation detection threshold that corresponds to a minimum modulation depth at which the user is able to perceive modulation of the spectro-temporally modulated audio signal, and determining, based on the modulation detection threshold, a hearing capability of the user. These and other operations that may be performed by system 100 are described herein.

System 100 may be implemented in any suitable manner as may serve a particular implementation. For example, system 100 may be implemented by one or more computing devices capable of presenting spectro-temporally modulated signals ("STMs") to a user (e.g., directly or by way of a speaker or receiver). To illustrate, system 100 may be implemented by a personal computer, a mobile device (e.g., a mobile phone configured to execute a mobile application that facilitates hearing capability evaluation), any of the hearing devices described herein, etc. In some examples, system 100 may be implemented at a clinician facility where an audiologist or the like uses system 100 to evaluate hearing loss characteristics of a user and uses those hearing loss characteristics to fit a hearing device to the user.

Figure 2:
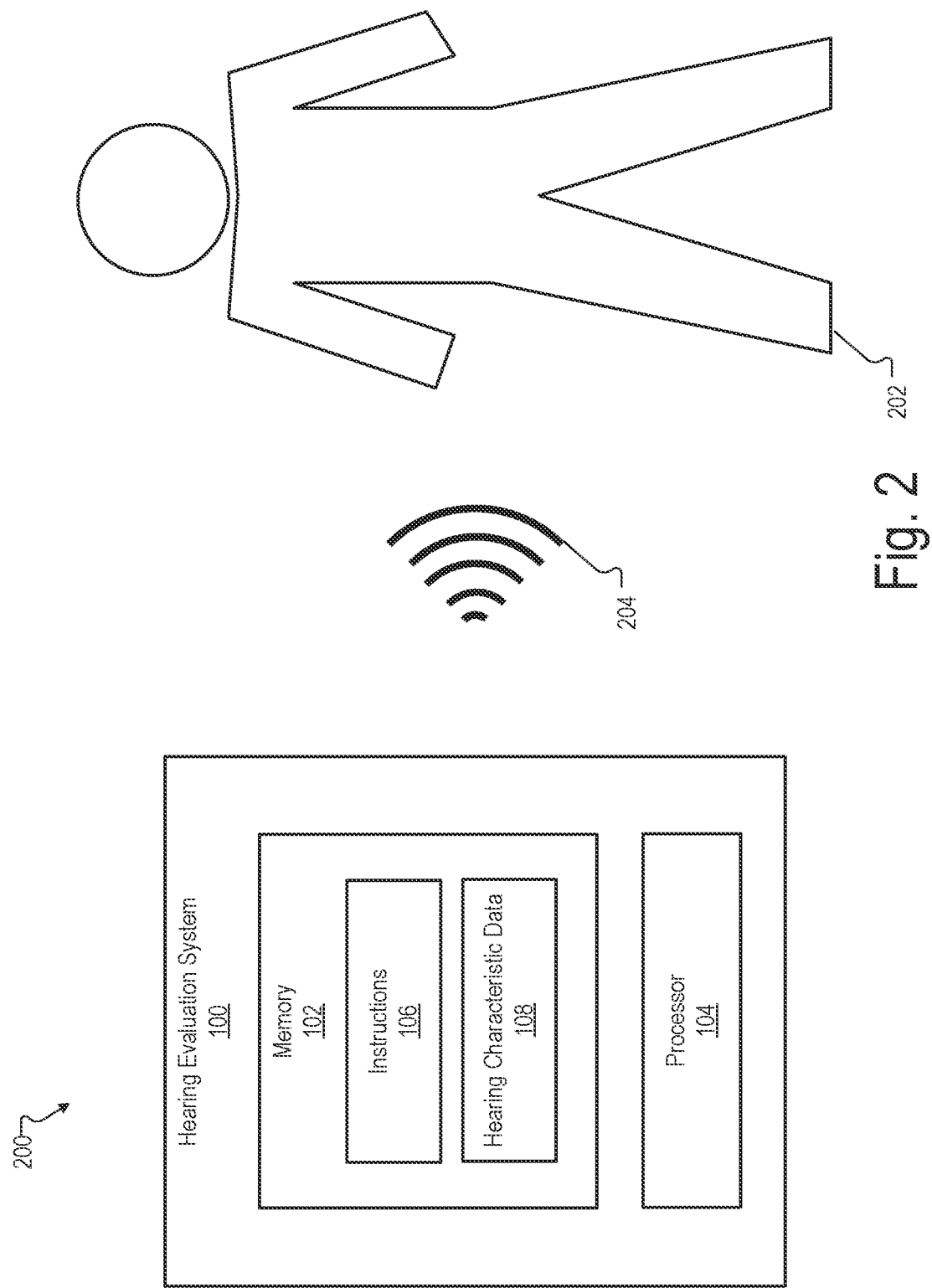
FIG. 2 illustrates an exemplary implementation of the hearing evaluation system of claim 1 according to principles described herein.

FIG. 2 shows an exemplary configuration 200 in which system 100 may be implemented. As shown in FIG. 2, system 100 may be provided in relation to a user 202 so as to present a spectro-temporally modulated ("STM") audio signal 204 to a user 202. To that end, system 100 may include or otherwise be communicatively connected to any suitable device configured to present audio content to user 202. For example, system 100 may include or otherwise be communicatively connected to a speaker (not shown) (e.g., an audiometer headphone, a loudspeaker, etc.) configured to present STM audio signal 204 to user 202. Additionally or alternatively, system 100 may direct a hearing device in any suitable manner to present (e.g., by way of a receiver of an ITE component) STM audio signal 204 to user 202 in certain implementations.

The audio characteristics of STM audio signal 204 may be defined in any suitable manner as may serve a particular implementation. Parameters used to define STM audio signal 204 may include, for example, a sampling rate parameter, a stimulus length parameter, a temporal modulation frequency parameter, a spectral modulation parameter (e.g., cycles/octave), a modulation depth parameter, a center frequency parameter, a bandwidth parameter, high and low cut off frequency parameters, and/or any other suitable parameter. System 100 may facilitate adjustment of such parameters in any suitable manner. For example, system 100 may provide one or more graphical user interfaces to facilitate a user (e.g., a clinician) adjusting one or more of such parameters to define STM audio signal 204 during a fitting procedure.

STM audio signal 204 may correspond to a broadband frequency range and may be spectrally modulated across any suitable range of the broadband frequency range. In certain examples, STM audio signal 204 may correspond to a broadband frequency range and may be spectrally modulated across the broadband frequency range. For example, STM audio signal 204 may be modulated substantially across an entire broadband frequency range (e.g., from 0 Hz to 15 kHz). In such examples, a modulation detection threshold determined based on STM audio signal 204 may correspond to a broadband modulation detection threshold. Such a broadband modulation detection threshold may be indicative of the hearing capability (e.g., spectral sensitivity and/or hearing thresholds) of user 202 with respect to the broadband frequency range. In addition, such a broadband modulation detection threshold may be used as an indicator for a maximum spectral sensitivity of the hearing of user 202 and may be used to estimate training effects.

In certain implementations, STM audio signal 204 may correspond to a broadband frequency range but may be modulated across only a sub-band frequency range within the broadband frequency range. STM audio signal 204 may be modulated across any suitable sub-band frequency range as may serve a particular implementation. For example, in certain implementations, the sub-band frequency range may be a one octave frequency band, a two octave frequency band, a three octave frequency band, a four octave frequency band, or any other suitable sub-band frequency range. In examples where STM audio signal 204 is modulated across a sub-band frequency range, the modulation detection threshold may be specific to the sub-band frequency range. In addition, the modulation detection threshold associated with a sub-band frequency range may be indicative of the hearing capability (e.g., spectral sensitivity and/or hearing thresholds) of user 202 with respect to the sub-band frequency range.

Figure 3:
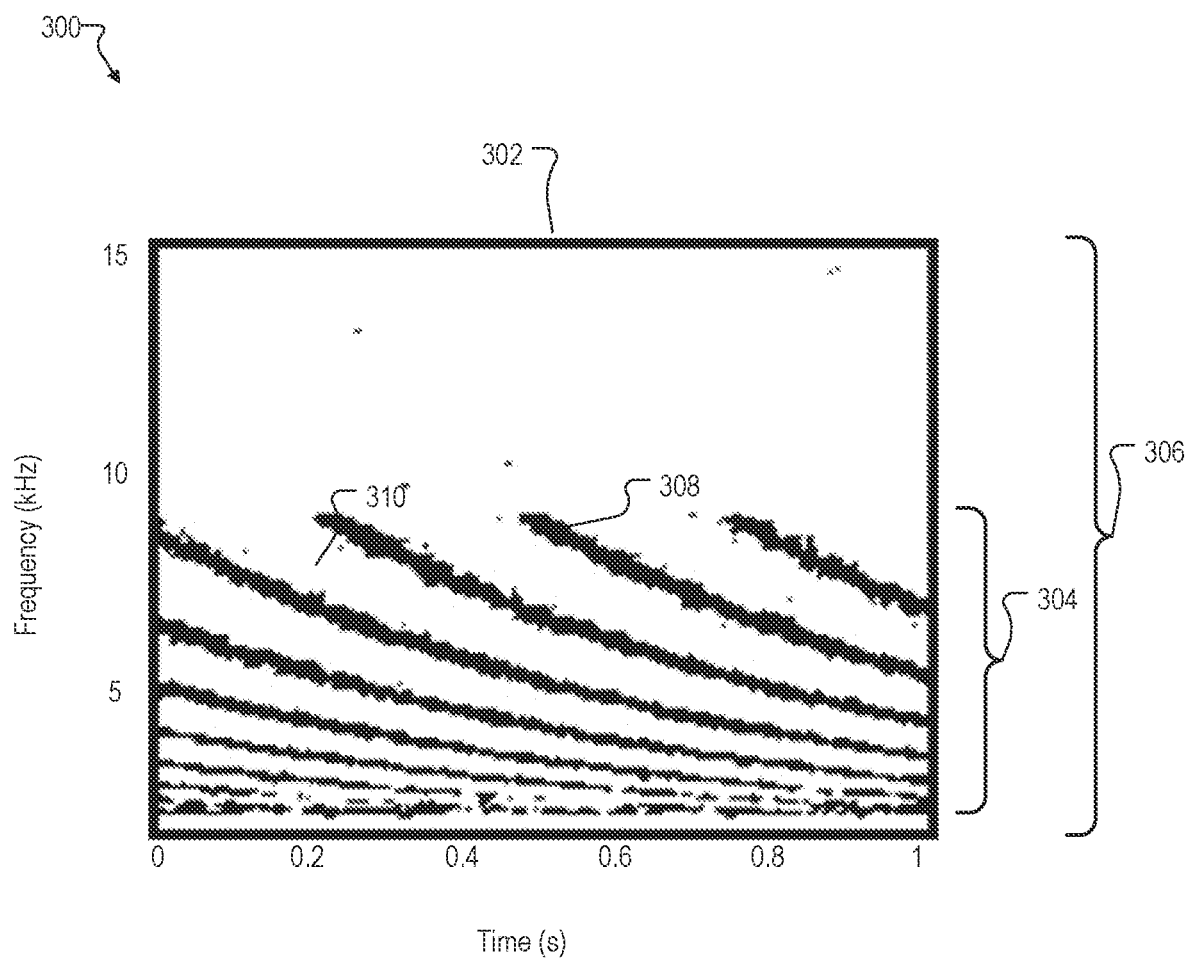
FIGS. 3 and 4 illustrate exemplary graphical depictions of spectro-temporally modulated audio signals according to principles described herein.

FIG. 3 shows an exemplary graphical depiction 302 that illustrates audio characteristics that STM audio signal 204 may have in certain implementations. As shown in FIG. 3, STM audio signal 204 may be modulated across a frequency domain shown along the y-axis and a time domain shown along the x-axis. In the example shown in FIG. 3, the following parameters are set for STM audio signal 204: a sampling frequency of 48000 Hz; a stimulation length 1 second; a temporal modulation frequency of 4 Hz; a spectral modulation of 2 cycles per octave; a modulation depth of 0 dB; a center frequency of 2000 Hz; a bandwidth of 4 octaves, a low cut off frequency of 500 Hz; and a high cut off frequency of 8000 Hz.

Figure 4:
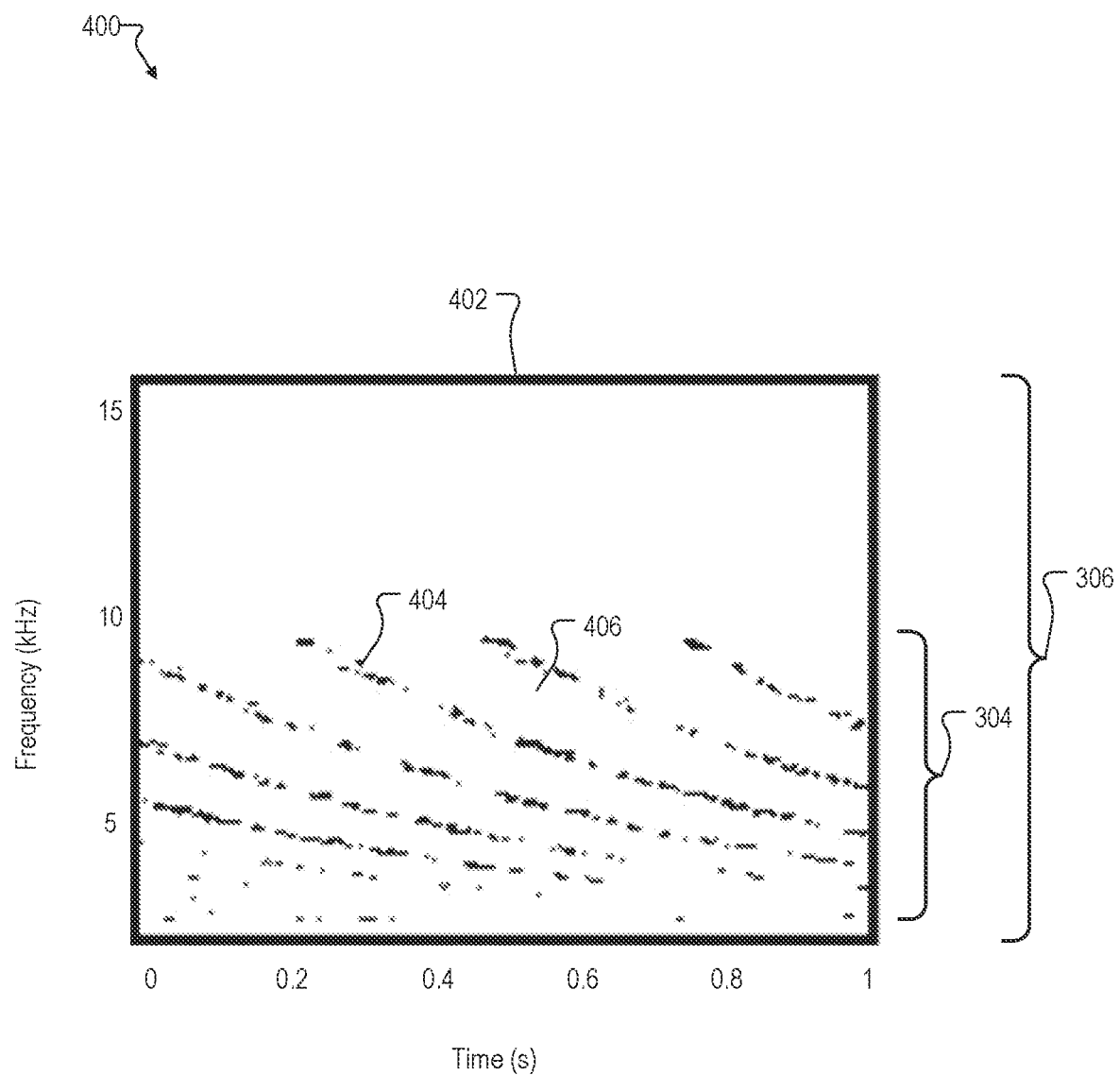

In the example shown in FIG. 3, STM audio signal is modulated across a sub-band frequency range 304 (as defined by low cut off frequency of 500 Hz and the high cut off frequency of 8000 Hz) within a broadband frequency range 306 of 0-15 kHz. STM audio signal 204 includes dark regions 308 and light regions 310 that are represented within sub-band frequency range 304. Dark regions 308 represent relatively higher intensity regions of STM audio signal 204 and light regions 310 represent relatively lower intensity regions of STM audio signal 204. Adjusting the modulation depth of STM audio signal 204 changes the relative intensity between the high intensity regions and the low intensity regions, thus making the modulation of STM audio signal 204 either easier for user 202 to perceive or more difficult for user 202 to perceive. To illustrate an example, the modulation depth of 0 dB in the example shown in FIG. 3 may be decreased, for example, to −10 dB. Such a change is illustrated in FIG. 4, which shows a graphical depiction 402 that includes dark regions 404 and light regions 406 within sub-band frequency range 304. As shown in FIG. 4, dark regions 404 are less pronounced as compared to dark regions 308 shown in FIG. 3 illustrating that the −10 dB modulation is less than that depicted in FIG. 3 and as a result the modulation represented in FIG. 4 may be more difficult for user 202 to perceive.

Figure 5:
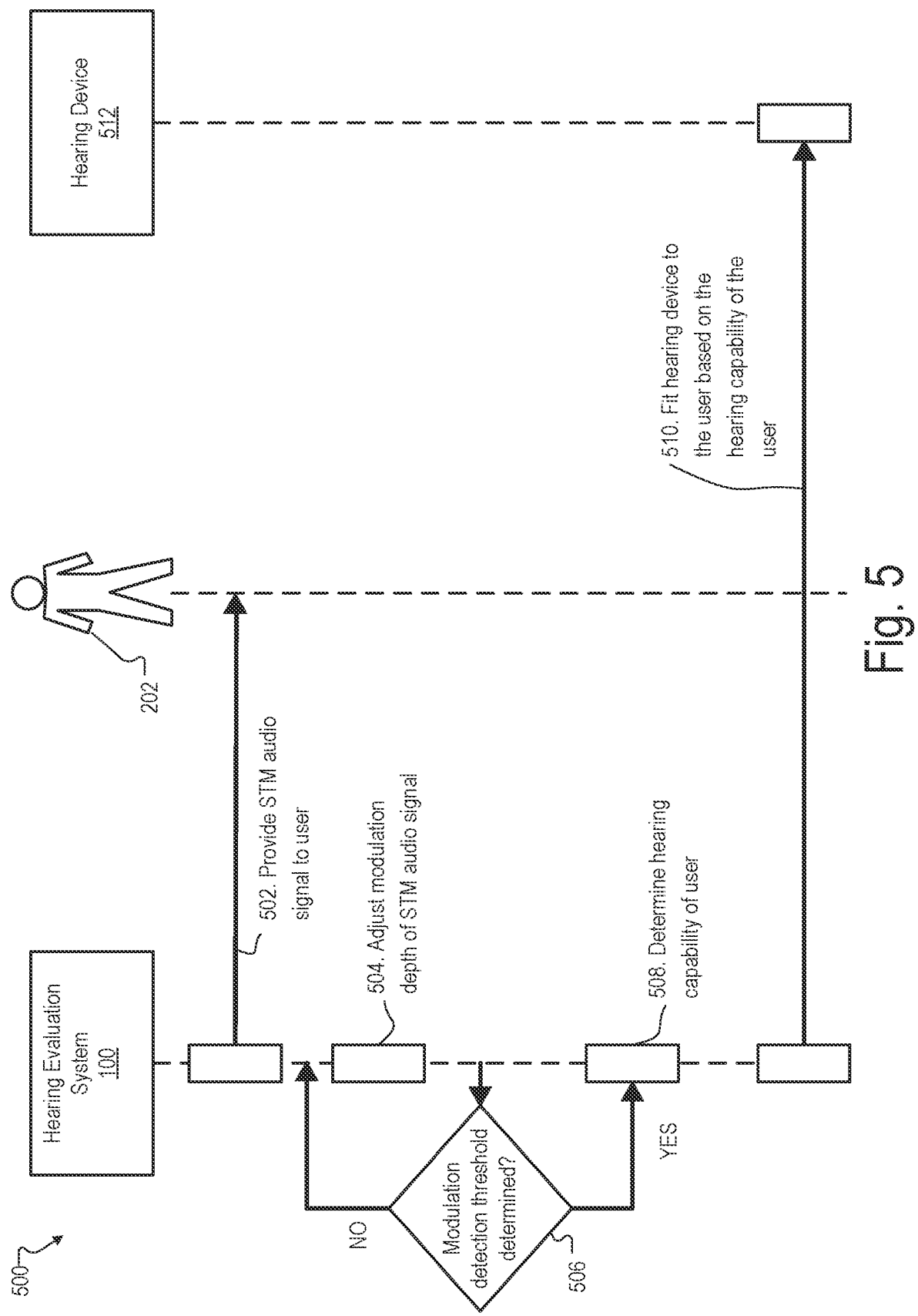
FIG. 5 illustrates an exemplary flowchart showing operations that may be performed by the hearing evaluation system of FIG. 1 according to principles described herein.

FIG. 5 shows an exemplary flowchart 500 that depicts operations that may be performed by system 100 (e.g., processor 104) according to principles described herein. As shown in FIG. 5, at operation 502 system 100 may present STM audio signal 204 to user 202. This may be performed in any suitable manner such as described herein. While STM audio signal 204 is presented to user 202, system 100 may adjust a modulation depth of STM audio signal 204. In certain examples, system 100 may adjust the modulation depth in response to an input provided by a clinician (e.g., by way of a graphical user interface). In certain alternative examples, system 100 may automatically adjust the modulation depth. As used herein, the expression "automatically" means that an operation (e.g., adjusting one or more parameters) or series of operations are performed without requiring further input from a user.

During adjustment of the modulation depth, system 100 may determine whether a modulation detection threshold has been reached at operation 506. This may be accomplished in any suitable manner. For example, system 100 may instruct user 202 in any suitable manner to indicate whether user 202 is able to perceive modulation of STM audio signal 204. System 100 may then receive subjective feedback from user 202 in the form of a communication indicating that user 202 is able to perceive the modulation of STM audio signal 204. To illustrate an example, system 100 may present an audio clip (e.g., by way of a headphone speaker) instructing user 202 to, for example, say "YES," raise a hand, and/or provide any other suitable communication to indicate that user 202 perceives the modulation. Based on the communication provided by user 202, system 100 may determine whether the modulation detection threshold has been reached.

If the answer at operation 506 is "NO," the process returns to before operation 504 and the modulation depth is adjusted again. System 100 may then perform operation 506 again to determine whether the modulation detection threshold has been determined at the adjusted modulation depth. This process may be repeated as many times as necessary until the modulation detection threshold is determined.

In certain examples, system 100 may adjust the modulation depth until user 202 perceives the modulation. For example, system 100 may initially set the modulation depth at a value that at which user 202 would not be able to perceive the modulation. System 100 may then facilitate incrementally increasing the modulation depth by any suitable amount until user 202 perceives the modulation. Alternatively, system 100 may adjust the modulation depth until user 202 stops perceiving the modulation. For example, system 100 may initially set the modulation depth at a value that at which user 202 would be able to perceive the modulation. System 100 may then facilitate incrementally decreasing the modulation depth by any suitable amount until user 202 begins perceiving the modulation.

If the answer at operation 506 is "YES," system 100 may determine a hearing capability (e.g., an individual spectral sensitivity and/or hearing thresholds) of user 202 based on the modulation detection threshold at operation 508. System 100 may determine the hearing capability of user 202 based on the modulation detection threshold in any suitable manner. For example, system 100 may compare the modulation detection threshold determined at operation 506 to one or more modulation detection thresholds of a person that has normal hearing characteristics within a frequency range associated with STM audio signal 204. In so doing, system 100 may facilitate defining frequency regions with relatively higher or lower spectral sensitivity and estimating the frequency dependent spectral sensitivity (also referred to as a frequency dependent resolution capability) of user 202 within those frequency regions.

System 100 may perform operations 502 through 508 any suitable number of times for different frequency ranges of a broadband frequency range. For example, system 100 may perform operations 502-508 for a broadband frequency range to determine a broadband modulation detection threshold. Additionally or alternatively, system 100 may perform operations 502 through 508 for any suitable number of sub-band frequency ranges included in a broadband frequency range. For example, system 100 may perform operations 502 through 508 for each of a broadband frequency range, a first sub-band frequency range included in a broadband frequency range, a second sub-band frequency range included in the broadband frequency range, and a third sub-band frequency range included in the broadband frequency range. The first, second, and third sub-band frequency ranges may each correspond to different sub-band frequency ranges within the broadband frequency range.

In certain examples, each sub-band frequency range may have the same size. For example, the first, the second, and the third sub-band frequency ranges in the example described above may each have a width of one octave. In such examples, each sub-band frequency range may correspond to a different one octave frequency band within the broadband frequency range. Alternatively, at least some of the sub-band frequency ranges may have different sizes. For example, the first sub-band frequency range may correspond to a four octave frequency band, and the second and third sub-band frequency ranges may correspond to different one octave frequency bands within the broadband frequency range.

In certain examples, system 100 may perform operations 502 through 508 any suitable number of times for progressively more narrow sub-band frequency ranges included in the broadband frequency range. In so doing, system 100 may facilitate increasing the frequency resolution of the measurement of the hearing capability of user 202 within certain target frequency regions of interest.

In certain examples, system 100 may select a sub-band frequency range to use to determine a modulation detection threshold based on a hearing profile (e.g., an audiogram) of user 202. Such a hearing profile may provide information regarding individual hearing thresholds and loudness comfort levels specific to user 202. To that end, system 100 may obtain a hearing profile of user 202 in any suitable manner. For example, in certain implementations system 100 may access a hearing profile that is already generated for user 202 from any suitable source. Alternatively, system 100 may facilitate generating a hearing profile for user 202 in any suitable manner.

As a result of repeating operations 502-508, system 100 may determine a broadband modulation detection threshold and one or more sub-band modulation detection thresholds. By determining both a broadband modulation detection threshold and one or more sub-band modulation detection thresholds (e.g., one octave modulation detection thresholds), it is possible to estimate the frequency dependent spectral sensitivity of user 202 relative to the determined modulation detection thresholds. This is advantageous in that systems and methods such as those described herein may be used without a training session and still provide feasible results.

In certain examples, operation 508 shown in FIG. 5 may include system 100 adding information associated with one or more modulation detection thresholds determined by way of operations 502-508 to a hearing profile of user 202. Such an addition may result in system 100 generating an augmented hearing profile that includes both hearing threshold data (e.g., generated based on pure-tone audiometry) and modulation detection threshold data (e.g., generated according to principles described herein).

Figure 6:
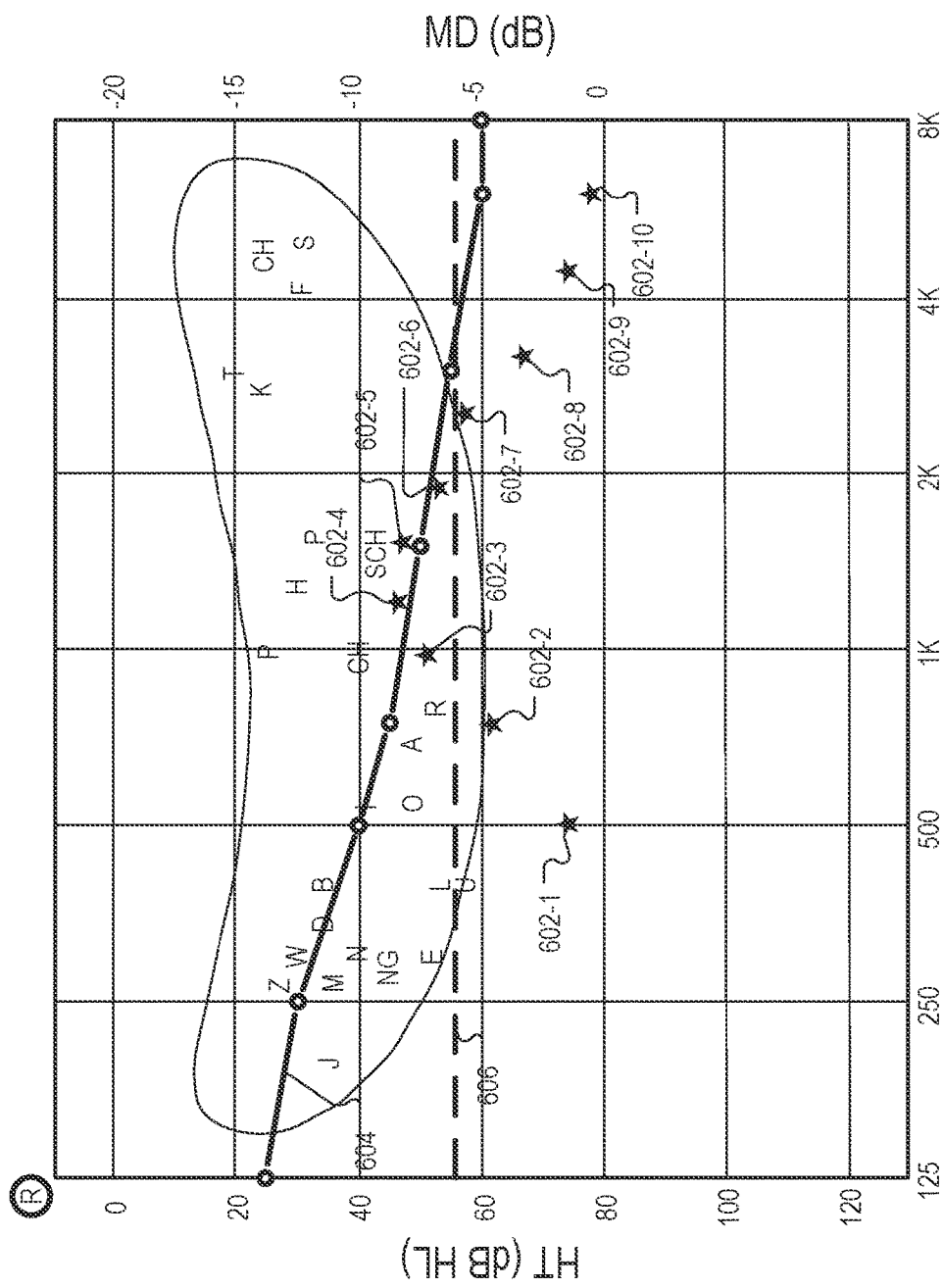
FIG. 6 illustrates an exemplary augmented individual hearing profile that includes modulation detection thresholds that may be determined according to principles described herein.

To illustrate, FIG. 6 shows an exemplary augmented hearing profile 600 that may be generated by system 100 according to principles described herein and may be provided for display during a fitting procedure. As shown in FIG. 6, hearing threshold in decibels (HL) is represented on the left side y-axis, frequency in Hz is represented along the x-axis, and modulation depth (MD) in decibels is represented along the right side y-axis. FIG. 6 includes a plurality indicators 602 (e.g., indicators 602-1 through 602-10) that each represent different determined modulation detection thresholds for user 202 at different frequencies. Although FIG. 6 shows ten indicators 602, it is understood that any suitable number of indicators representing modulation detection thresholds may be depicted in an augmented hearing profile as may serve a particular implementation.

Line 604 in FIG. 6 represents hearing thresholds for user 202 at different frequencies. The hearing threshold values represented by line 604 may be determined in any suitable manner using pure-tone audiometry. Dashed line 606 represents half of a broadband modulation detection threshold.

In the example shown in FIG. 6, an "R" is provided at the upper left corner of augmented hearing profile 600. The "R" indicates that augmented hearing profile 600 is specific to the hearing loss characteristics of the right ear of user 202. It is understood that system 100 may additionally or alternatively generate another augmented hearing profile that is specific to hearing loss characteristics of the left ear of user 202 and that may be separately provided for display during a fitting procedure. Alternatively, such hearing loss characteristics for the left ear may be provided for display together with the hearing loss characteristics of the right ear in augmented hearing profile 600.

Returning to FIG. 5, at operation 510, system 100 may fit a hearing device 512 to user 202 based on the hearing capability (e.g., individual spectral sensitivity and/or hearing thresholds) determined at operation 508. Although only one hearing device 512 is shown in FIG. 5, it is understood that hearing device 512 may be included in a system that includes more than one hearing device configured to provide or enhance hearing to a user. For example, hearing device 512 may be included in a binaural hearing system that includes two hearing devices, one for each ear. In such examples, hearing device 512 may be provided behind, for example, the left ear of the user and an additional hearing device may be provided behind the right ear of the user. When hearing device 512 is included as part of a binaural hearing system, hearing device 512 may communicate with the additional hearing device by way of a binaural communication link that interconnects hearing device 512 with the additional hearing device. Such a binaural communication link may include any suitable wireless or wired communication link as may serve a particular implementation.

Figure 7:
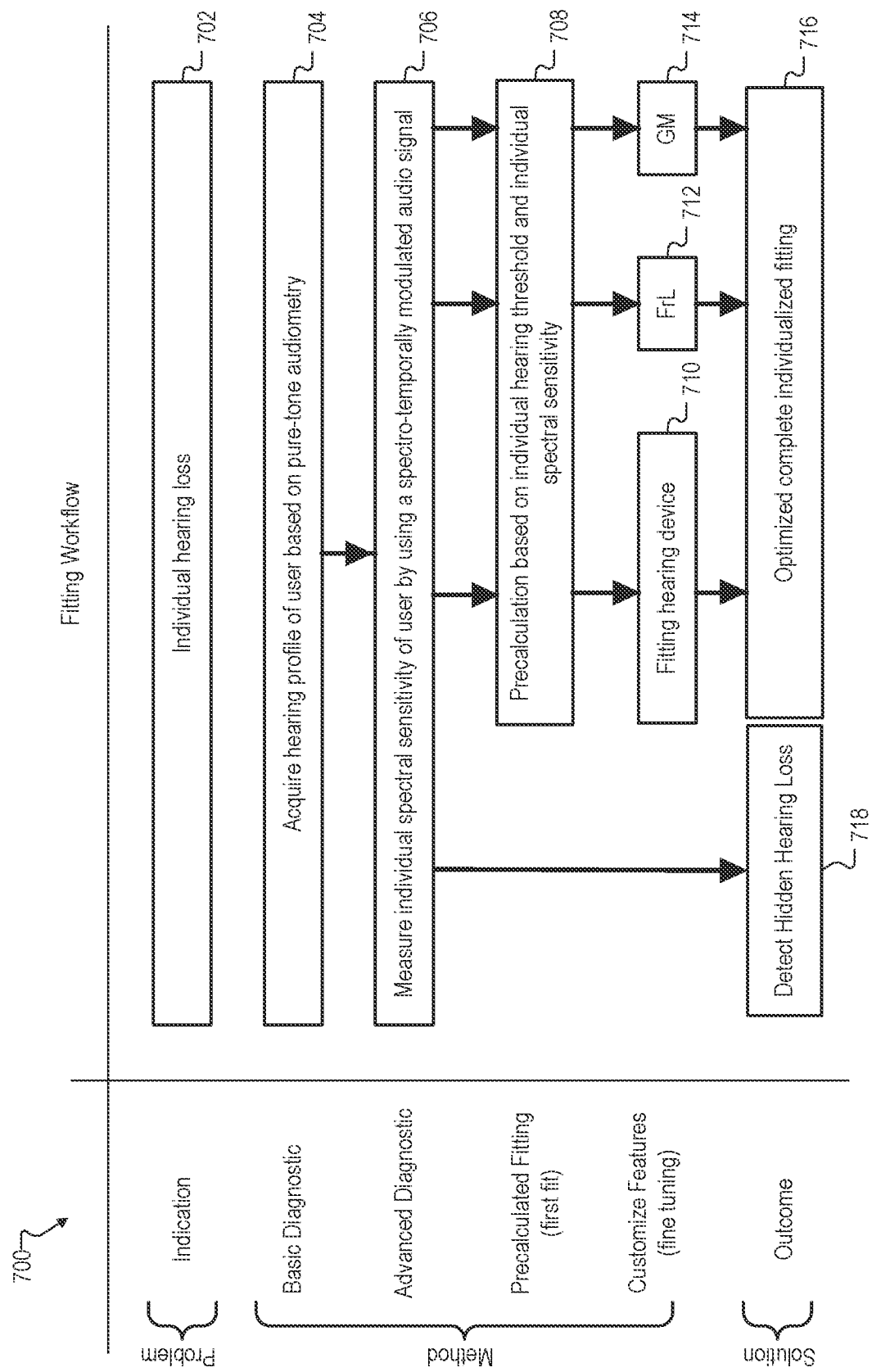
FIG. 7 illustrates an exemplary hearing device fitting workflow depicting exemplary hearing device fitting operations that may be performed according to principles described herein.

System 100 may fit hearing device 512 to user 202 in any suitable manner. For example, according to principles described herein, system 100 may facilitate determining the individual frequency dependent spectral sensitivity of user 202. System 100 may then use the individual frequency dependent spectral sensitivity to adjust one or more fitting parameters of hearing device 512 for any suitable number of different frequency regions. To illustrate, system 100 may determine that user 202 has a first spectral sensitivity in a first frequency region, a second spectral sensitivity in a second frequency region, and a third spectral sensitivity in a third frequency region. System 100 may adjust one or more fitting parameters of hearing device 512 with respect to the first frequency region based on the first spectral sensitivity. Likewise, system 100 may adjust one or more fitting parameters of hearing device 512 with respect to the second and third frequency regions based on the second and third spectral sensitivities. As such, system 100 may specifically individualize fitting of hearing device 512 to user 202 in different frequency regions based on the individual frequency dependent spectral sensitivity of user 202. FIG. 7 shows an exemplary fitting workflow 700 depicting fitting operations that may be performed by system 100 according to principles described herein. As shown in FIG. 7, workflow block 702 represents an indication regarding the individual hearing loss of user 202.

Workflow block 704 represents a basic diagnostic operation that includes acquiring (e.g., generating or obtaining from any suitable source) a hearing profile that is specific to user 202 and that is generated based on pure-tone audiometry.

Workflow block 706 represents an advanced diagnostic operation in which individual spectral sensitivity of user 202 is measured by using an STM audio signal (e.g., STM audio signal 204) in any suitable manner such as described herein.

Workflow block 708 represents a precalculated fitting operation that may be performed by system 100 based on both the individual hearing thresholds and the individual spectral sensitivity of user 202.

Workflow block 710 represents a fitting operation in which hearing device 512 is fit to user 202 based on the individual hearing thresholds and individual spectral sensitivity of user 202.

Workflow block 712 represents a frequency lowering algorithm that may be applied in certain examples to fit hearing device 512 to user 202. Such a frequency lowering algorithm may be used to restore audibility of high frequencies for a user. To accomplished this, frequency lowering algorithms are generally configured to map higher frequencies, that are predicted to be inaudible to a user, to lower frequencies that are predicted to be audible. System 100 may implement any suitable type of frequency lowering algorithm as may serve a particular implementation. Exemplary types of frequency lowering algorithms may include non-linear frequency compression, adaptive non-linear frequency compression, linear frequency compression, frequency transposition, frequency composition, dynamic spectral identification and translation, or any other suitable type frequency lowering algorithm.

In certain examples, system 100 may modify a frequency lowering algorithm based on the individual hearing threshold and/or the individual spectral sensitivity of user 202. For example, system 100 may obtain a hearing profile of user 202 in any suitable manner. Based on the hearing profile, system 100 may determine a frequency region of an input audio signal and/or an output audio signal to be subjected to the frequency lowering algorithm. System 100 may then adjust a parameter of the frequency lowering algorithm based on one or more modulation detection thresholds determined at workflow block 706.

System 100 may adjust any suitable parameter of the frequency lowering algorithm based on the one or more modulation detection thresholds as may serve a particular implementation. For example, system 100 may adjust or change a target frequency region of an output audio signal to be subjected to the frequency lowering algorithm in any suitable manner based on the individual frequency dependent spectral sensitivity of user 202. In certain examples, system 100 may adjust the frequency lowering algorithm such that the frequency lowering algorithm acts stronger or is more aggressive when a target frequency region shows a relatively high spectral sensitivity. On the other hand, when the spectral sensitivity in a target frequency region is relatively low, system 100 may reduce a compression ratio/amount of frequency mapping, increase a start frequency and work with a stronger amplification of mapped frequencies in a source region instead, and/or shift a target frequency region to even lower frequencies where spectral sensitivity may be higher.

Workflow block 714 represents a gain model that may be additionally or alternatively applied to at least part of the broadband frequency range based on the individual hearing threshold and/or the individual spectral sensitivity of user 202. In such examples, system 100 may adjust, based on one or more modulation detection thresholds determined at workflow block 706, a parameter of the gain model implemented by a hearing device to facilitate fitting the hearing device to user 202. System 100 may adjust a parameter of the gain model in any suitable manner as may serve a particular implementation. For example, system 100 may implement the gain model more aggressively in certain target frequency regions having high spectral sensitivity thereby increasing resolution of the dynamic range for the hearing impaired.

Workflow block 716 represents a complete individualized fitting of a hearing device to user 202 based on workflow block 710 and, in certain examples, one or more of workflow blocks 712 and 714.

In certain examples, the individual spectral sensitivity measured at workflow block 706 may be useful to detect hidden hearing loss of user 202. In certain examples, such hidden hearing loss may be caused due to damage to inner and/or outer hair cells and nerve fibers of user 202. For example, the inner hair cells of user 202 may be partially damaged in a particular frequency region. Such damage may not be discernable from the hearing thresholds of user 202 indicated in a hearing profile (e.g., an audiogram) because neighboring auditory filters may mask the damage in the frequency region. However, a relatively higher modulation detection threshold than is normal in the frequency region may be indicative of the damage and may be used to detect the hidden hearing loss. By detecting such hidden hearing loss, it is possible to detect slight hearing loss earlier than may otherwise be possible. This may result in an earlier decision by user 202 to seek help from a hearing care professional, which is beneficial because the earlier a hearing impaired person decides to get a hearing device, the better the hearing impaired person is able to adapt to and use the hearing device.

Additionally or alternatively, the individual spectral sensitivity measured at workflow block 706 may be useful to provide an estimation regarding particular damage to inner and/or outer hair cells of user 202. For example, a reduced spectral sensitivity when the sound itself is still perceivable at a moderate stimulus level could indicate that the hearing loss is mainly caused by damaged inner hair cells. However, a high or normal spectral sensitivity at loud stimulus levels but an increased hearing threshold could indicate damaged outer hair cells but mainly intact inner hair cells. This would allow an estimation of whether a simple amplification of a sound is enough for user 202 or whether adjusting one or more other fitting parameters would be useful. Such an estimation could also help in evaluating whether user 202 should receive a cochlear implant or not and whether any respective parts of the cochlear implant should be omitted from an implanted electrode to conserve residual hearing of user 202.

In examples where hearing device 512 corresponds to a cochlear implant, system 100 may additionally or alternatively use the individual spectral sensitivity determined at workflow block 706 to estimate a quality of connection of a cochlear implant electrode to an auditory nerve. For example, one or more modulation detection thresholds such as those described herein may provide information regarding which frequency regions of the cochlear implant electrode have a good connection to the auditory nerve. System 100 may then use such information in any suitable manner to fine tune fitting of the cochlear implant to user 202.

In certain examples, the hearing capability of a user may additionally or alternatively correspond to one or more hearing thresholds of the user. This is possible based on a correlation that exists between modulation detection thresholds such as those described herein and hearing thresholds of a user. A modulation detection threshold may be correlated with a hearing threshold in any suitable manner. For example, a modulation detection threshold below a predefined value within a certain sub-band frequency range may be indicative of the user having a hearing threshold below a predefined value within that sub-band frequency range, which may be indicative of hearing loss. In such examples, system 100 may additionally or alternatively be configured to estimate one or more hearing thresholds of a user based on one or more modulation detection thresholds. Estimating hearing thresholds based on modulation thresholds may be beneficial in circumstances where it is not possible to measure such hearing thresholds in a conventional way (e.g., by using pure-tone audiometry). For example, in noisy environments (e.g., in public places, at home, at work, etc.) where browser-based or application-based hearing screenings may be performed, the background noise may make it difficult or impossible to use audio tones to adequately detect hearing thresholds. However, modulation detection thresholds such as those described herein may be independent of presentation level as long as the modulation carrier noise is perceivable. Accordingly, in such circumstances, system 100 may be configured to estimate a hearing threshold of a user based on a determined modulation detection threshold.

In certain examples, the estimation of a hearing threshold based on a modulation detection threshold may correspond to a preliminary or rough estimate of potential hearing loss of the user. In such examples, system 100 may provide a notification to the user in any suitable manner that informs the user of the potential hearing loss and instructs the user to schedule a hearing test with a hearing care professional such as an audiologist or the like at a hearing device fitting facility.

The preceding disclosure describes adjusting modulation depth of an STM audio signal to facilitate determining a modulation detection threshold. In such examples, other parameters (e.g., the bandwidth, low and high cut off frequencies, etc.) used to define the STM audio signal may be fixed while the modulation depth is adjusted. However, it is understood that different parameters may be adjusted while other parameters are fixed in other implementations. For example, in certain alternative implementations, the bandwidth may be varied at a fixed modulation depth. In such examples, the modulation detection threshold may depend on the adjusted bandwidth instead of the adjusted modulation depth.

Figure 8:
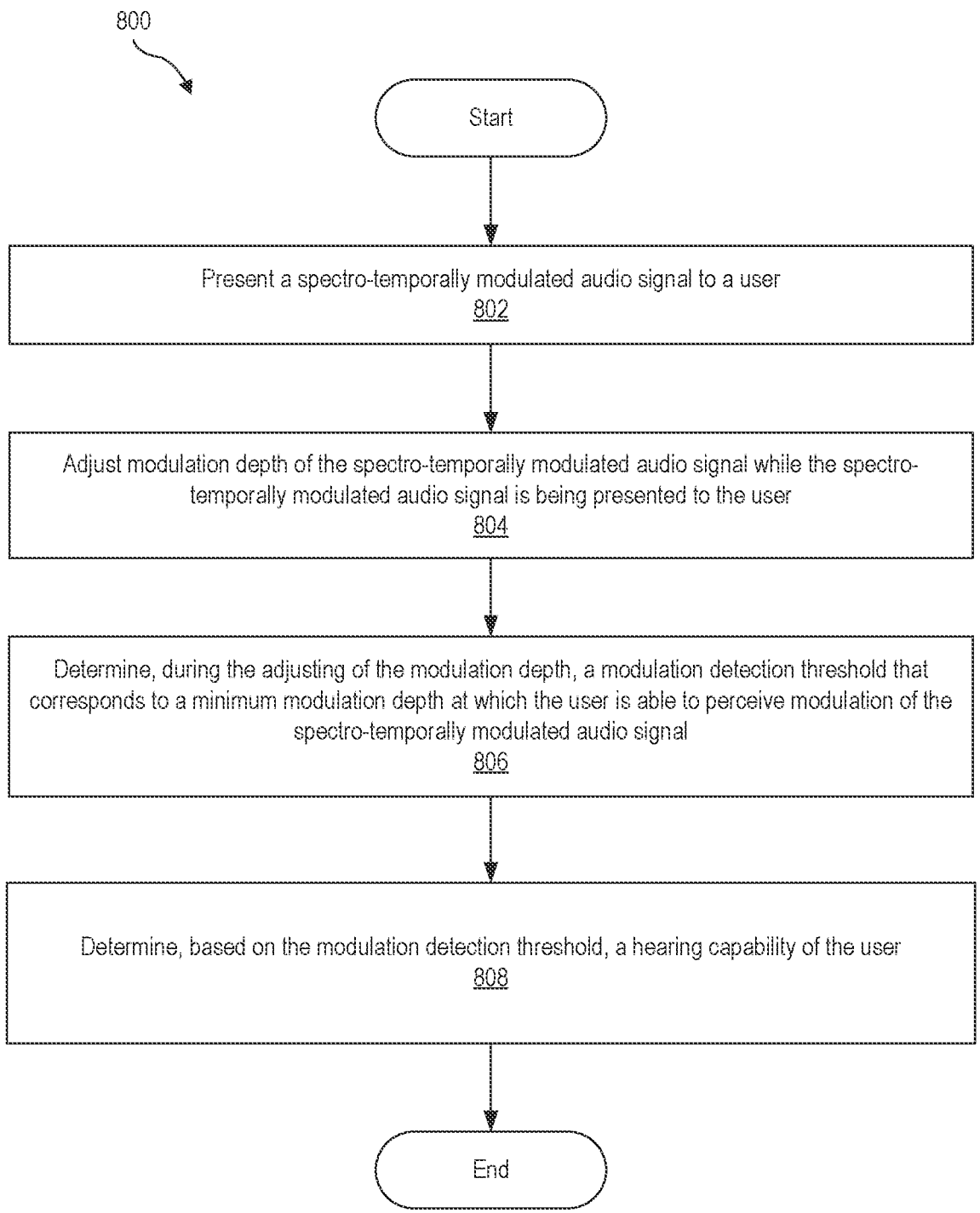
FIG. 8 illustrates an exemplary method implementing a spectro-temporally modulated audio signal according to principles described herein.

FIG. 8 illustrates an exemplary method 800 for implementing a spectro-temporally modulated audio signal. While FIG. 8 illustrates exemplary operations according to one embodiment, other embodiments may omit, add to, reorder, and/or modify any of the operations shown in FIG. 8. One or more of the operations shown in FIG. 8 may be performed by a hearing evaluation system such as hearing evaluation system 100, any components included therein, and/or any implementation thereof.

At operation 802, a processor (e.g., processor 104) may present a spectro-temporally modulated audio signal to a user (e.g., user 202). As described herein the spectro-temporally modulated audio signal may be modulated in both a frequency domain and a time domain. Operation 802 may be performed in any of the ways described herein. For example, the spectro-temporally modulated audio signal may be presented to the user with a modulation depth specified by a clinician and/or hearing evaluation system 100.

At operation 804, the processor may adjust a modulation depth of the spectro-temporally modulated audio signal while the spectro-temporally modulated audio signal is being presented to the user. Operation 804 may be performed in any of the ways described herein.

At operation 806, the processor may determine, during the adjusting of the modulation depth, a modulation detection threshold that corresponds to a minimum modulation depth at which the user is able to perceive modulation of the spectro-temporally modulated audio signal. Operation 806 may be performed in any of the ways described herein.

At operation 808, the processor may determine, based on the modulation detection threshold, a hearing capability of the user. For example, the processor may determine a frequency dependent spectral sensitivity of the user based on the modulation detection threshold. Operation 808 may be performed in any of the ways described herein.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 9:
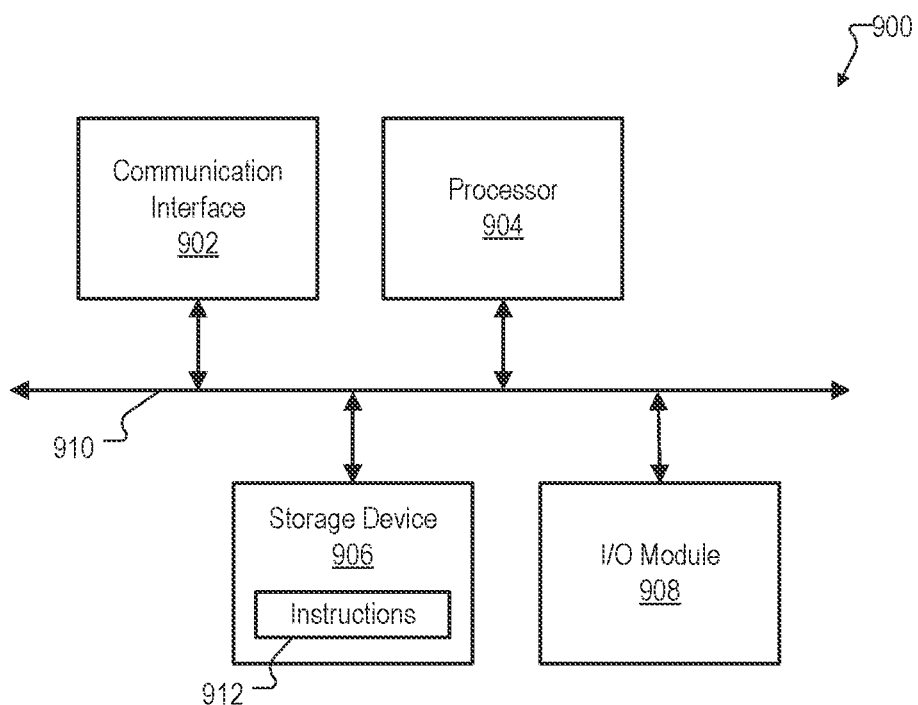
FIG. 9 illustrates an exemplary computing device according to principles described herein.

FIG. 9 illustrates an exemplary computing device 900 that may be specifically configured to perform one or more of the processes described herein. As shown in FIG. 9, computing device 900 may include a communication interface 902, a processor 904, a storage device 906, and an input/output ("I/O") module 908 communicatively connected one to another via a communication infrastructure 910. While an exemplary computing device 900 is shown in FIG. 9, the components illustrated in FIG. 9 are not intended to be limiting. Additional or alternative components may be used in other embodiments. Components of computing device 900 shown in FIG. 9 will now be described in additional detail.

Communication interface 902 may be configured to communicate with one or more computing devices. Examples of communication interface 902 include, without limitation, a wired network interface (such as a network interface card), a wireless network interface (such as a wireless network interface card), a modem, an audio/video connection, and any other suitable interface.

Processor 904 generally represents any type or form of processing unit capable of processing data and/or interpreting, executing, and/or directing execution of one or more of the instructions, processes, and/or operations described herein. Processor 904 may perform operations by executing computer-executable instructions 912 (e.g., an application, software, code, and/or other executable data instance) stored in storage device 906.

Storage device 906 may include one or more data storage media, devices, or configurations and may employ any type, form, and combination of data storage media and/or device. For example, storage device 906 may include, but is not limited to, any combination of the non-volatile media and/or volatile media described herein. Electronic data, including data described herein, may be temporarily and/or permanently stored in storage device 906. For example, data representative of computer-executable instructions 912 configured to direct processor 904 to perform any of the operations described herein may be stored within storage device 906. In some examples, data may be arranged in one or more databases residing within storage device 906.

I/O module 908 may include one or more I/O modules configured to receive user input and provide user output. I/O module 908 may include any hardware, firmware, software, or combination thereof supportive of input and output capabilities. For example, I/O module 908 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 908 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 908 is configured to provide graphical data to a display for presentation to a user. The graphical data may be representative of one or more graphical user interfaces and/or any other graphical content as may serve a particular implementation.

In some examples, any of the systems, hearing devices, and/or other components described herein may be implemented by computing device 900. For example, memory 102 may be implemented by storage device 906, and processor 104 may be implemented by processor 904.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
a memory storing instructions; and
a processor communicatively coupled to the memory and configured to execute the instructions to:
present a spectro-temporally modulated audio signal to a user, the spectro-temporally modulated audio signal modulated within both a frequency domain and a time domain;
adjust a modulation depth of the spectro-temporally modulated audio signal while the spectro-temporally modulated audio signal is being presented to the user;
determine, during the adjusting of the modulation depth, a modulation detection threshold that corresponds to a minimum modulation depth at which the user is able to perceive modulation of the spectro-temporally modulated audio signal; and
determine, based on the modulation detection threshold, a hearing capability of the user.

2. The system of claim 1, wherein the hearing capability of the user is at least one of a spectral sensitivity of the user or a hearing threshold of the user.

3. The system of claim 1, wherein:
the spectro-temporally modulated audio signal corresponds to a broadband frequency range and is spectrally modulated across the broadband frequency range; and
the modulation detection threshold is indicative of the hearing capability of the user with respect to the broadband frequency range.

4. The system of claim 1, wherein:
the spectro-temporally modulated audio signal corresponds to broadband frequency range and is spectrally modulated across only a sub-band frequency range within the broadband frequency range;
the modulation detection threshold is specific to the sub-band frequency range; and
the modulation detection threshold is indicative of the hearing capability of the user with respect to the sub-band frequency range.

5. The system of claim 4, wherein the processor is further configured to execute the instructions to:
obtain a hearing profile of the user; and
select the sub-band frequency range based on the hearing profile of the user.

6. The system of claim 4, wherein the sub-band frequency range is a one octave frequency band within the broadband frequency range.

7. The system of claim 4, wherein the processor is further configured to execute the instructions to:
spectrally modulate, after determining the modulation detection threshold, the spectro-temporally modulated audio signal across only an additional sub-band frequency range within the broadband frequency range, the additional sub-band frequency range different than the sub-band frequency range;
adjust the modulation depth of the spectro-temporally modulated audio signal while the spectro-temporally modulated audio signal is being presented to the user and modulated across the additional sub-band frequency range;
determine, during the adjusting of the modulation depth, an additional modulation detection threshold that corresponds to a minimum modulation depth at which the user is able to perceive the modulation of the spectro-temporally modulated audio signal while modulated across the additional sub-band frequency range; and
determine, based on the additional modulation detection threshold, a hearing capability of the user with respect to the additional sub-band frequency range.

8. The system of claim 1, wherein the adjusting of the modulation depth includes increasing the modulation depth until the user perceives the modulation.

9. The system of claim 1, wherein the adjusting of the modulation depth includes decreasing the modulation depth until the user stops perceiving the modulation.

10. The system of claim 1, wherein the determining of the modulation detection threshold includes:
instructing the user to indicate when the user begins perceiving the modulation of the spectro-temporally modulated audio signal;
receiving a communication from the user indicating when the user begins perceiving the modulation of the spectro-temporally modulated audio signal; and
determining the modulation detection threshold based on the communication provided by the user.

11. The system of claim 1, wherein the processor is further configured to execute the instructions to fit a hearing device to the user based on the hearing capability of the user.

12. The system of claim 11, wherein:
the processor is further configured to execute the instructions to obtain a hearing profile of the user; and
the fitting of the hearing device to the user includes:
determining, based on the hearing profile of the user, a frequency region of an input audio signal to be subjected to a frequency lowering algorithm; and
adjusting one or more parameters of the frequency lowering algorithm based on the modulation detection threshold.

13. The system of claim 11, wherein the fitting of the hearing device to the user includes adjusting, based on the modulation detection threshold, one or more parameters of a gain model implemented by the hearing device.

14. A method comprising:
presenting, by a hearing evaluation system, a spectro-temporally modulated audio signal to a user, the spectro-temporally modulated audio signal modulated within both a frequency domain and a time domain;
adjusting, by the hearing evaluation system, a modulation depth of the spectro-temporally modulated audio signal while the spectro-temporally modulated audio signal is being presented to the user;
determining, by the hearing evaluation system, during the adjusting of the modulation depth, a modulation detection threshold that corresponds to a minimum modulation depth at which the user is able to perceive modulation of the spectro-temporally modulated audio signal; and
determining, by the hearing evaluation system based on the modulation detection threshold, a hearing capability of the user.

15. The method of claim 14, wherein the hearing capability of the user is a spectral sensitivity of the user.

16. The method of claim 14, wherein:
the spectro-temporally modulated audio signal corresponds to a broadband frequency range and is spectrally modulated across only a sub-band frequency range within the broadband frequency range;
the modulation detection threshold is specific to the sub-band frequency range; and
the modulation detection threshold is indicative of the hearing capability of the user within the sub-band frequency range.

17. The method of claim 14, wherein the determining of the modulation detection threshold includes:
instructing the user to indicate when the user begins perceiving the modulation of the spectro-temporally modulated audio signal;
receiving a communication from the user indicating when the user begins perceiving the modulation of the spectro-temporally modulated audio signal; and
determining the modulation detection threshold based on the communication provided by the user.

18. The method of claim 14, further comprising:
obtaining, by the hearing evaluation system, a hearing profile of the user; and
fitting, by the hearing evaluation system, a hearing device to the user based on the hearing capability of the user and the hearing profile,
wherein the fitting of the hearing device to the user includes:
determining, based on the hearing profile of the user, a frequency region of an input audio signal to be subjected to a frequency lowering algorithm; and
adjusting one or more parameters of the frequency lowering algorithm based on the modulation detection threshold.

19. The method of claim 14, further comprising:
obtaining, by the hearing evaluation system, a hearing profile of the user; and
fitting, by the hearing evaluation system, a hearing device to the user based on the hearing capability of the user and the hearing profile,
wherein the fitting of the hearing device to the user includes:
determining, based on the hearing profile of the user, a frequency region of an output audio signal to be subjected to a frequency lowering algorithm; and
adjusting one or more parameters of the frequency lowering algorithm based on the modulation detection threshold.

20. A non-transitory computer readable storage medium storing instructions that, when executed, direct a processor to:
present a spectro-temporally modulated audio signal to a user, the spectro-temporally modulated audio signal modulated within both a frequency domain and a time domain;
adjust a modulation depth of the spectro-temporally modulated audio signal while the spectro-temporally modulated audio signal is being presented to the user;

determine, during the adjusting of the modulation depth, a modulation detection threshold that corresponds to a minimum modulation depth at which the user is able to perceive modulation of the spectro-temporally modulated audio signal; and determine, based on the modulation detection threshold, a hearing capability of the user.

\* \* \* \* \*